United States Patent
Gkikas et al.

(10) Patent No.: US 12,178,878 B2
(45) Date of Patent: Dec. 31, 2024

(54) AMYLOID PEPTIDE SCAFFOLDS COORDINATE WITH ALZHEIMER'S DISEASE DRUGS

(71) Applicants: The University of Massachusetts, Boston, MA (US); The Texas A&M University System, College Station, TX (US)

(72) Inventors: Manos Gkikas, Brighton, MA (US); Phanourios Tamamis, College Station, TX (US); Sai Jonnalagadda, College Station, TX (US)

(73) Assignees: THE UNIVERSITY OF MASSACHUSETTS, Boston, MA (US); THE TEXAS A&M UNIVERSITY SYSTEM, College Station, TX (US)

( * ) Notice: Subject to any disclaimer, the term of this patent is extended or adjusted under 35 U.S.C. 154(b) by 84 days.

(21) Appl. No.: 17/292,045

(22) PCT Filed: Nov. 8, 2019

(86) PCT No.: PCT/US2019/060454
§ 371 (c)(1),
(2) Date: May 7, 2021

(87) PCT Pub. No.: WO2020/097455
PCT Pub. Date: May 14, 2020

(65) Prior Publication Data
US 2024/0197893 A1    Jun. 20, 2024

Related U.S. Application Data

(60) Provisional application No. 62/757,384, filed on Nov. 8, 2018.

(51) Int. Cl.
A61K 47/64    (2017.01)
A61K 47/69    (2017.01)

(52) U.S. Cl.
CPC .......... *A61K 47/64* (2017.08); *A61K 47/6953* (2017.08)

(58) Field of Classification Search
None
See application file for complete search history.

(56) References Cited

U.S. PATENT DOCUMENTS 6,245,572 B1    6/2001    Wall
2011/0171312 A1    7/2011    Kuo et al.

OTHER PUBLICATIONS

Brooks, B. et al.; "CHARMM: The Biomolecular Simulation Program"; Journal of Computational Chemistry, vol. 30, Issue No. 10; 2009; pp. 1545-1614.

Burley, S. et al.; "RCSB Protein Data Bank: biological macromolecular structures enabling research and education in fundamental biology, biomedicine, biotechnology and energy"; Nucleic Acids Research, vol. 47; Database Issue; 2019; pp. D464-D474; doi: 10.1093/nar/gky1004.

International Search Report and Written Opinion for International Application PCT/US2019/060454; International Filing Date: Nov. 8, 2019; Date of Mailing: Apr. 8, 2020; 11 pages.

Trott, O. et al.; "AutoDock Vina: improving the speed and accuracy of docking with a new scoring function, efficient optimization and multithreading"; Journal of Computational Chemistry, vol. 31, Issue No. 2; 2010; pp. 455-461.

*Primary Examiner* — Sergio Coffa
(74) *Attorney, Agent, or Firm* — CANTOR COLBURN LLP

(57) ABSTRACT

A complex includes an amyloid peptide complexed with a cholinesterase inhibitor, an NMDA receptor antagonist, or a combination, of a cholinesterase inhibitor and an NMDA receptor antagonist, wherein the amyloid peptide comprises $X_1X_2GAIIGX_3X_4$ (SEQ ID NO: 2), wherein $X_1$ and $X_4$ are each independently YF or FY, and $X_2$ and $X_3$ are each 1 amino acid long, and are each independently T, N, S, or Q; or $X_2$ and $X_3$ are each 2 amino acid long and $X_2$ is (Y or F)T, (Y or F)N, (Y or F)S or (Y or F)Q, and $X_3$ is T(Y or F), N(Y or F), S(Y or F) or Q(Y or F), wherein the amyloid peptide self-assembles into amyloid fibrils, and wherein the peptide has a total length of 11-13 amino acids.

9 Claims, 5 Drawing Sheets

Specification includes a Sequence Listing.

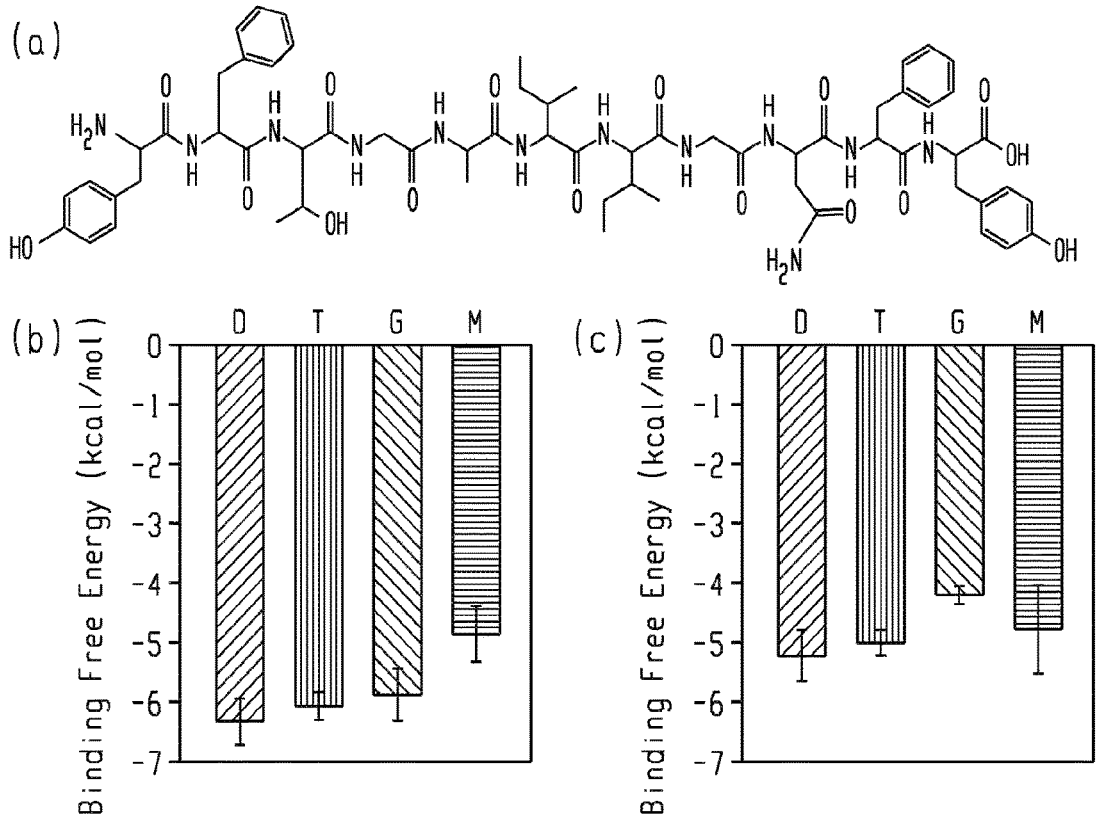
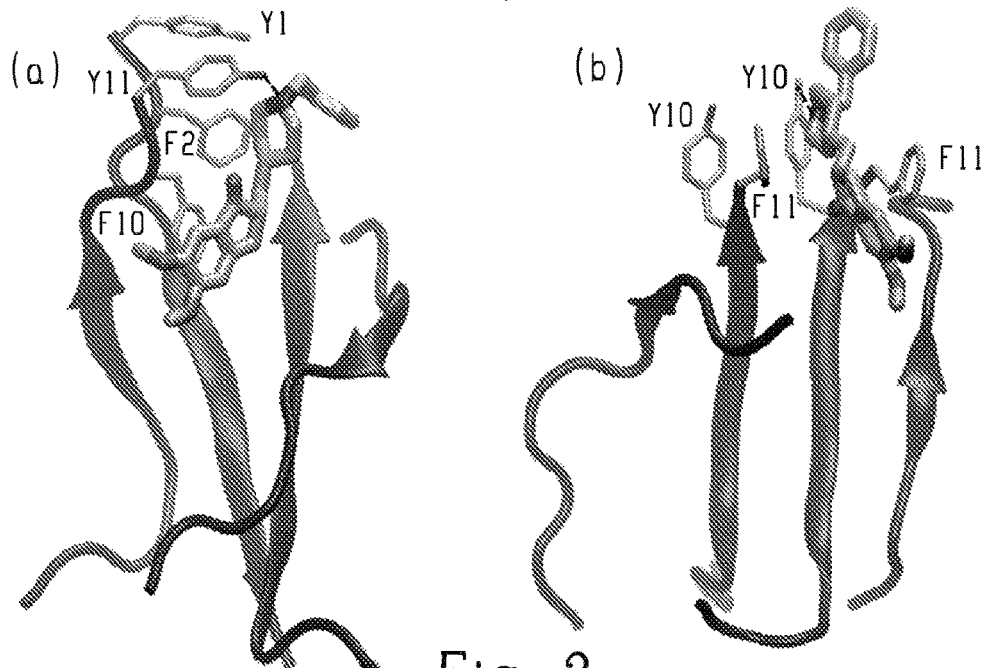
Fig. 1
Fig. 2

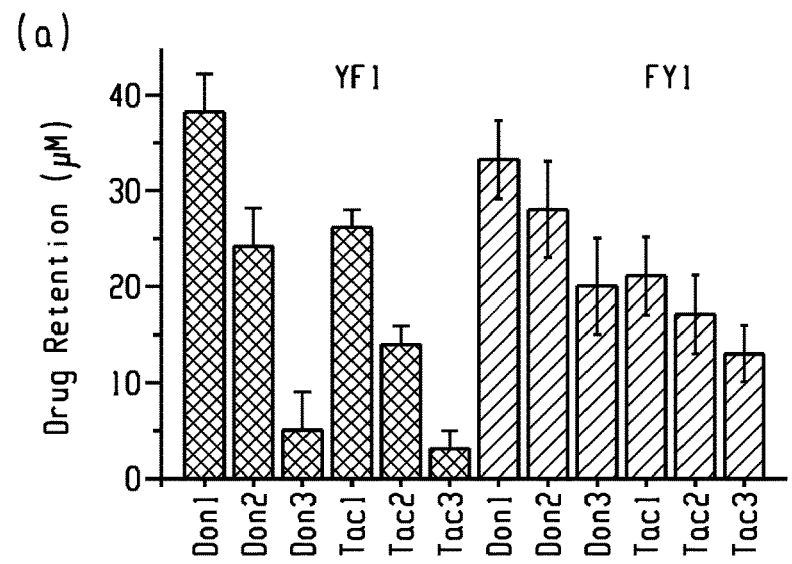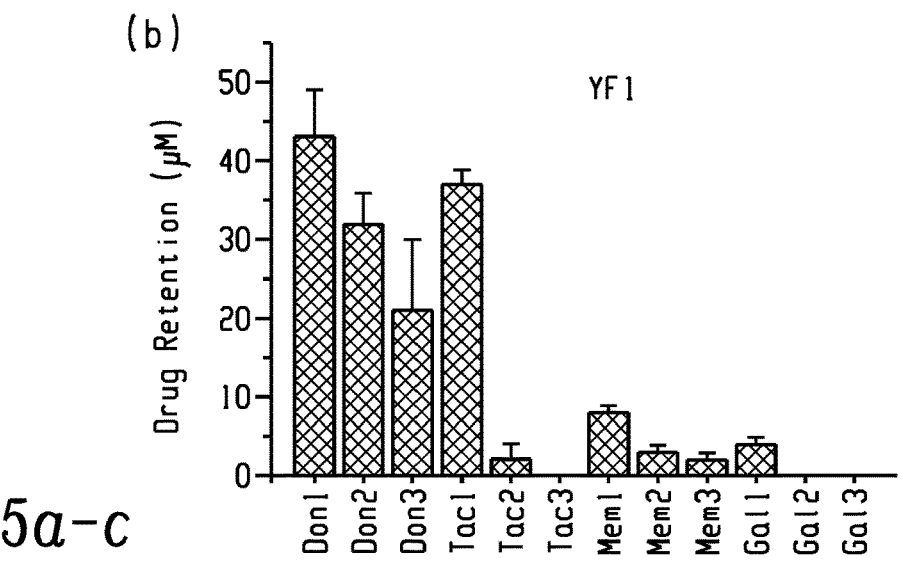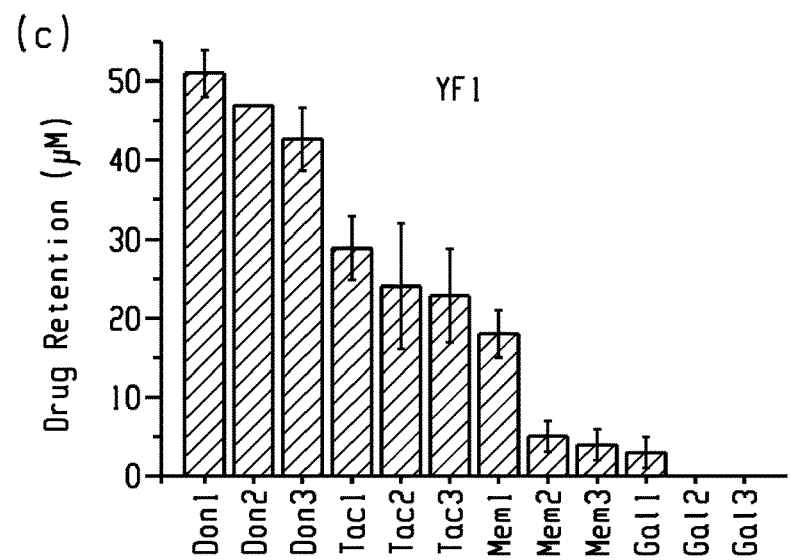
Fig. 5a-c

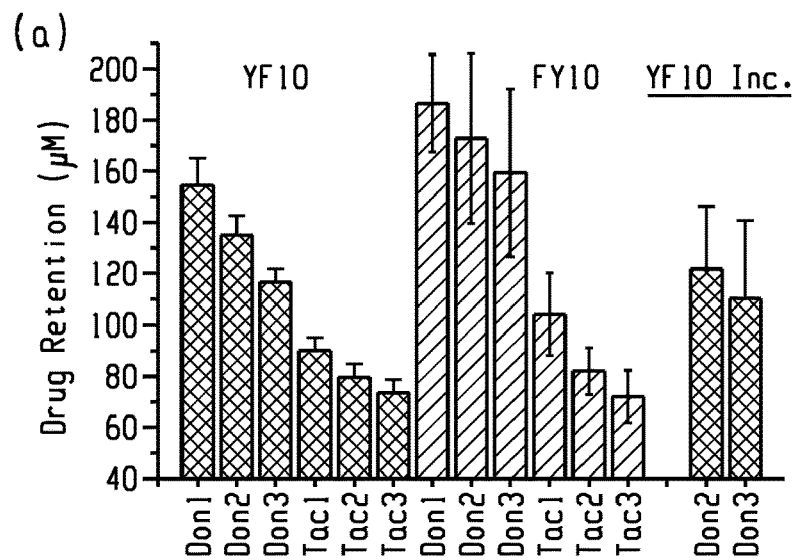
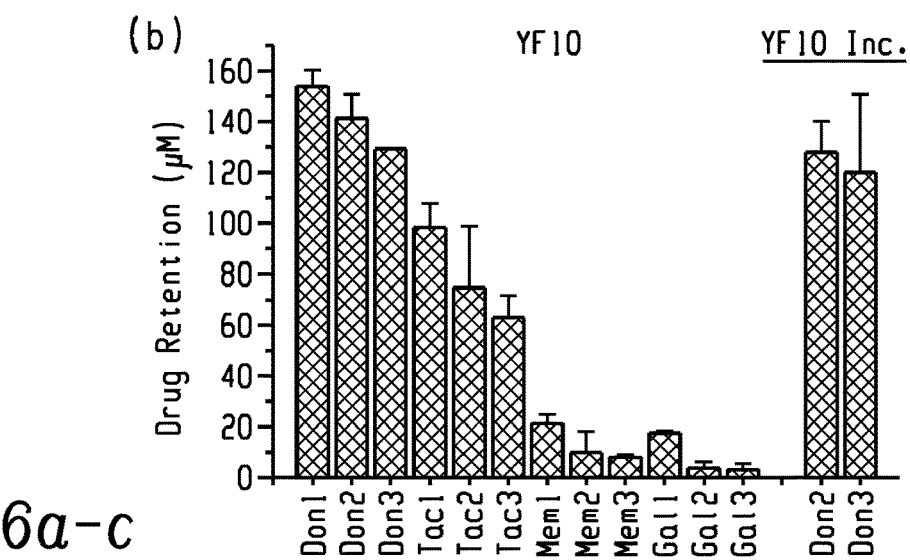
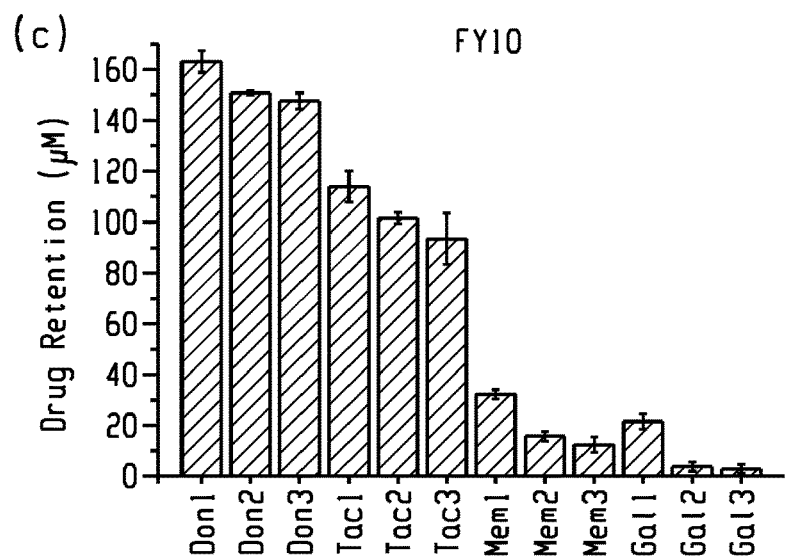
Fig. 6a-c

AMYLOID PEPTIDE SCAFFOLDS COORDINATE WITH ALZHEIMER'S DISEASE DRUGS

CROSS REFERENCE TO RELATED APPLICATIONS

This application is a National Stage application of PCT/US2019/060454, filed Nov. 8, 2019, which claims the benefit of priority to U.S. Provisional Application 62/757,384, filed Nov. 8, 2018, both of which are incorporated by reference in their entirety herein.

SEQUENCE LISTING

The Instant Application contains a Sequence Listing which has been submitted electronically in ASCII format and is hereby incorporated by reference in its entirety. Said ASCII copy, created on Nov. 12, 2021 is named "Replacement Sequence List (TXT) UM10019US2 (UML 2019-008; TAMUS-4993)" and is 1,945 bytes in size.

FIELD OF THE DISCLOSURE

The present disclosure is related to novel methods for the delivery of drugs for the treatment of neurodegenerative diseases such as Alzheimer's disease.

BACKGROUND

Alzheimer's disease (AD) is an irreversible neurodegenerative disorder that develops slowly and worsens over time, characterized by progressive deterioration of cognitive behavior and functionality that impairs significantly the activities of daily life. AD is strongly related to acetylcholine (ACh), a neurotransmitter, which is released by nerve cells to transfer signals to other cells, related to memory, motivation, language, and muscle contraction. A characteristic of AD is the low concentration of ACh in AD patients that makes neuro connection between cholinergic synapses extremely difficult. Donepezil, galantamine, rivastigmine, memantine, and a donepezil/memantine combination are currently administered to patients (approved AD drugs) depending on the progression stage. The first three drugs are acetyl cholinesterase inhibitors, while memantine is an N-methyl-D-aspartate (NMD A) receptor antagonist that blocks the NMDA receptors (glutamate receptors and ion channel proteins) found in nerve cells, reducing the glutamate neuroactivity.

Butyryl- and acetylcholinesterase (BChE and AChE) inhibitors block the enzyme in the cholinergic system, allowing for higher accumulation of the neurotransmitter ACh in synapses, and therefore higher cognition. Though the aforementioned AD drugs (4±1 cocktail) have been approved for clinical use by the U.S. Food and Drug Administration (FDA), modest and transient therapeutic effects have been witnessed so far, while minimal-to-negligible cognition is confessed by neurologists, caregivers, and primary care providers, most likely due to the short half-life of the inhibitors. Formulations that could enhance the effectivity of current marketed AD drugs and their delivery to the target enzyme are an option for stabilizing or even enhancing cognition.

What is needed are improved formulations for the treatment of neurodegenerative diseases such as AD.

BRIEF SUMMARY

In one aspect, a complex comprises an amyloid peptide complexed with a cholinesterase inhibitor, an NMDA receptor antagonist, or a combination of a cholinesterase inhibitor and an NMDA receptor antagonist, wherein the amyloid peptide comprises X1X2GAIIGX3X4 (SEQ ID NO: 2), wherein Xi and $X_4$ are each independently YF or FY, and $X_2$ and $X_3$ are each 1 amino acid long, and are each independently T, N, S, or Q; or $X_2$ and $X_3$ are each 2 amino acid long and $X_2$ is (Y or F)T, (Y or F)N, (Y or F)S or (Y or F)Q, and $X_3$ is T(Y or F), N(Y or F), S(Y or F) or Q(Y or F), wherein the amyloid peptide self-assembles into fibrils, and wherein the peptide has a total length of 11-13 amino acids.

In another aspect, a pharmaceutical composition comprises the foregoing complex and a pharmaceutically acceptable excipient.

A method of treating a neurodegenerative disease comprises administering the foregoing complex to a subject in need thereof.

BRIEF DESCRIPTION OF THE DRAWINGS

FIG. 1a-c. FIG. 1a shows the chemical structure of the amyloid peptide carrier YFTGAIIGNFY (SEQ ID NO: 4). FIG. 1b and FIG. 1c represent computationally predicted binding free energies for (D) donepezil, (T) tacrine, (G) galantamine, and (M) memantine in complex with the designed peptides YFTGAIIGNFY (SEQ ID NO: 4) and FYTGAIIGNYF (SEQ ID NO: 3).

FIGS. 2a-b show molecular graphic images of the computationally predicted binding mode of donepezil in complex with the designed peptides YFTGAIIGNFY (SEQ ID NO: 4) and FYTGAIIGNYF (SEQ ID NO: 3). FIG. 2a shows a computationally docked binding mode of donepezil binding to YFTGAIIGNFY (SEQ ID NO: 4). FIG. 2b shows a computationally docked binding mode of donepezil binding to FYTGAIIGINYF (SEQ ID NO: 3).

FIG. 3a shows a computationally docked binding mode of tacrine binding to YFTGAIIGNFY (SEQ ID NO: 4). FIG. 3b shows a computationally docked binding mode of tacrine binding to FYTGAIIGNYF (SEQ ID NO: 3).

FIG. 5a-c show AD drug quantification upon capturing by amyloid peptides YFTGAIIGNFY (SEQ ID NO: 4) (black) and FYTGAIIGNYF (SEQ ID NO: 3) (patterned) at 1 mg/mL at washings 1-3, as assessed by (5a) UV-Vis and (5b), (5c) MRM-MS.

FIGS. 6a-c show AD drug quantification upon capturing by amyloid peptides YFTGAIIGNFY (SEQ ID NO: 4) (black) and FYTGAIIGNYF (SEQ ID NO: 3) (patterned) at 5 mg/mL at washings 1-3, as assessed by (6a) UV-Vis and (6b), (6c) MRM-MS. YFTGAIIGNFY/Donepezil at 5 mg/mL incubated at 37° C. in PBS for one day is also shown (highlighted black).

Figure 3:
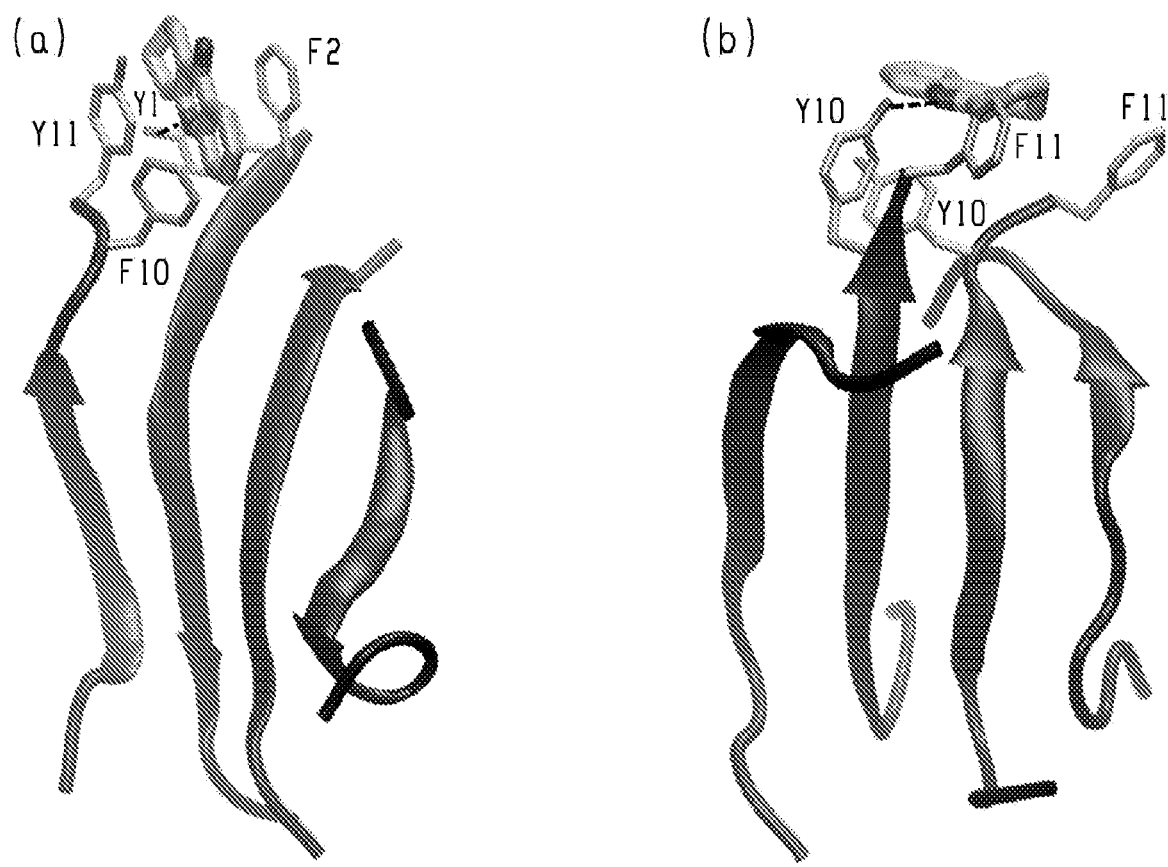
FIGS. 3 a-b show molecular graphic images of the computationally predicted binding mode of tacrine in complex with the designed peptides YFTGAIIGNFY (SEQ ID NO: 4) and FYTGAIIGNYF (SEQ ID NO: 3.

The above-described and other features will be appreciated and understood by those skilled in the art from the following detailed description, drawings, and appended claims.

DETAILED DESCRIPTION

Naturally occurring or engineered amyloids have been reported to bind ions or compounds. Yet, the functionalization of amyloid materials to bind to certain compounds (e.g., drugs) is not straightforward and has proven challenging to achieve, relying primarily on intuition as to which modifications can transform an amyloid into a functional material. As a result, the exploitation of amyloid materials as carriers for the therapeutic-sustained release of drugs has been significantly limited due to (i) the scarcity of studies on amyloid peptide fibrils with exposed non-P-sheet forming residues at the termini, and (ii) until recently, the lack of computational methods for designing such functional amyloid materials tailored to bind to certain compounds.

GAIIG (SEQ ID NO: 1) was shown to be an amyloidogenic core of YATGAIIGNII (SEQ ID NO: 6) according to Kokotidou et al (FEBS Lett. 2018; 592(11): 1777-1788), which can self-assemble into amyloid fibrils which can constitute amyloid designable scaffolds, incorporating mutable non-P-sheet forming residues. These structures were used as an input in a computational protocol for the design of functional amyloid materials binding to certain compounds. The protocol was used in the past by Jonnalagadda et al (J Phys Chem B. 2018; 122(30):7555-7568) to design amyloid materials binding to cesium ions, and here, the protocol has been further advanced and implemented for the design of amyloid materials binding to certain compounds of medical interest, such as key cognitive AD drugs, including donepezil, tacrine, galantamine and memantine.

Described herein is the design of functional amyloid materials binding to AD drugs as novel drug delivery carriers, aiming to enhance the half-life and efficacy of current AD drugs and potentially the stabilization of cognition. Motivated by the amyloids' reported biocompatibility, and their ability to be modified at a sequence level, so as to bind to one or combinations of AD drugs with high affinity, amyloid materials were hypothesized that they could constitute a highly promising direction for delivering AD drugs. The hypothesis that a single amyloid material can bind all the four AD drugs was tested by computationally designing and experimentally testing the capacity of two of the engineered functional amyloid materials, containing the GAIIG (SEQ ID NO: 1) amyloid core and flanking functional amino acids on both sides, to bind to four AD drugs. Among others, it is shown that the amyloid peptide-based transport system coordinates with AD drugs and stabilizes them, with higher capturing and binding affinity to be shown for tacrine and donepezil. The complexation is effective in both dilute solutions as well as at higher peptide concentrations yielding AD drug-containing fibrils, while the binding is shown to be effective even after multiple aqueous washings or after incubation. Such amyloid peptide/AD drug biomaterial formulations could be potentially administered orally, transdermally, or intranasally, targeting directly the enzyme.

It has been shown herein that designed amyloid materials bind to four AD drugs. This study presents the first functional amyloid materials that can bind AD drugs, by mimicking the mechanism by which the same AD drugs bind to proteins according to experimentally resolved structures, including the target enzyme AChE, which is part of the inhibition mechanism for three of the four AD drugs investigated. The highest binding capacity is shown for donepezil and tacrine, while memantine and galantamine show moderate-to-low binding, in line with computational predictions of binding free energies.

Overall, the computationally designed amyloid peptide scaffolds, encompassing a GAIIG (SEQ ID NO: 1) amylogenic core and mutable non-P-sheet forming residues at the termini, are experimentally shown (by both UV-Vis and MS) to coordinate with AD drugs in dilute (FIG. 5) and concentrated (fibril-forming) peptide solutions (FIG. 6), with tacrine and donepezil to show the highest capturing. Strong and stable capturing is shown for some of the AD drugs even after extensive subsequent aqueous washings, as well as after incubation at physiological conditions, denoting high coordination efficiency by the designed amyloid peptides.

In an aspect, a complex comprises an amyloid peptide non-covalently (physically) complexed with a cholinesterase inhibitor, an NMDA receptor antagonist, or a combination of a cholinesterase inhibitor and an NMDA receptor antagonist, wherein the amyloid peptide comprises $X_1X_2GAIIGX_3X_4$ (SEQ ID NO: 2), wherein $X_1$ and $X_4$ are each independently YF or FY, and $X_2$ and $X_3$ are each 1 amino acid long, and are each independently T, N, S, or Q; or $X_2$ and $X_3$ are each 2 amino acid long and $X_2$ is (Y or F)T, (Y or F)N, (Y or F)S or (Y or F)Q, and $X_3$ is T(Y or F), N(Y or F), S(Y or F) or Q(Y or F), wherein the amyloid peptide self-assembles into fibrils, and wherein the peptide has a total length of 11-13 amino acids.

As used herein, the transitional term "comprises" means that the amyloid peptide is as defined, but other elements may be added and still form a construct within the scope of the claim, so long as X1-X4 are as defined, and the peptide self-assembles into amyloid fibrils at higher peptide concentration or can be used in dilute solution (low peptide concentration) and binds a cholinesterase inhibitor, an NMDA receptor antagonist, or both. Exemplary additional elements include N-terminus or C-terminus modifications, amino acid protecting groups at the termini, and detectable labels such as fluorescent or phosphorescent labels or molecular imaging probes such as contrast agents for X-ray imaging, PET scan, SPECT scan or radioisotopes.

It was shown by the inventors through computational-based design confirmed through experimental work that short peptides containing an amyloidogenic core and having FY or YF at the termini are particularly useful for complexing cholinesterase inhibitors and NMDA receptor antagonists.

In an aspect, a complex comprises an amyloid peptide complexed with a cholinesterase inhibitor, an NMDA receptor antagonist, or a combination of a cholinesterase inhibitor and an NMDA receptor antagonist, wherein the amyloid peptide consists essentially of $X_1X_2GAIIGX_3X_4$ (SEQ ID NO: 2), wherein $X_1$ and $X_4$ are each independently YF or FY, and $X_2$ and $X_3$ are each 1 amino acid long, and are each independently T, N, S, or Q; or $X_2$ and $X_3$ are each 2 amino acid long and $X_2$ is (Y or F)T, (Y or F)N, (Y or F)S or (Y or F)Q, and $X_3$ is T(Y or F), N(Y or F), S(Y or F) or Q(Y or F), wherein the amyloid peptide self-assembles into fibrils, and wherein the peptide has a total length of 11-13 amino acids.

As used herein, the transitional term "consists essentially of" means that the amyloid peptide may include elements that do not materially affect the basic and novel characteristic of the claimed peptides, that is, so long as X1-X4 are as defined, and the amyloid peptide self-assembles into amyloid fibrils and binds a cholinesterase inhibitor, an NMDA receptor antagonist, or both. Exemplary additional elements include those described above.

In yet another aspect, a complex comprises an amyloid peptide complexed with a cholinesterase inhibitor, an NMDA receptor antagonist, or a combination of a cholinesterase inhibitor and an NMDA receptor antagonist,
wherein the amyloid peptide consists of
$X_1X_2GAIIGX_3X_4$ (SEQ ID NO: 2), wherein
$X_1$ and $X_4$ are each independently YF or FY, and
$X_2$ and $X_3$ are each 1 amino acid long, and are each independently T, N, S, or Q; or $X_2$ and $X_3$ are each 2 amino acid long and $X_2$ is (Y or F)T, (Y or F)N, (Y or F)S or (Y or F)Q, and $X_3$ is T(Y or F), N(Y or F), S(Y or F) or Q(Y or F),
wherein the amyloid peptide self-assembles into fibrils, and wherein the peptide has a total length of 11-13 amino acids.

As used herein, the transitional term "consists of" means that the amyloid peptides are those specifically defined in the claims with no modifications.

Exemplary cholinesterase inhibitors include donepezil, galantamine, rivastigmine, tacrine, neostigmine, and edrophonium. Exemplary NMDA receptor antagonists include memantine, amantadine, ketamine, dizoclopine, or d-cycloserine.

In an aspect, in dilute peptide solution (low peptide concentration such as 1 mg/ml), the drug complexes with the peptide without prior amyloid self-assembly. At high peptide concentration (e.g., >5 mg/ml), the amyloid peptides can be assembled and then the drug is added to form the complex.

Also included herein are pharmaceutical compositions comprising the complexes and a pharmaceutically acceptable excipient, such as diluents, preservatives, solubilizers, emulsifiers, and adjuvants. As used herein "pharmaceutically acceptable excipients" are well known to those skilled in the art.

The complex may be made into a form for oral administration, such as a tablet or syrup, for example.

For topical application to the skin, the complex may be made up into a cream, lotion or ointment including hydrogel formulations. Cream or ointment formulations which may be used for the drug are conventional formulations well known in the art. Topical administration includes transdermal formulations such as patches.

For topical application to the eye, the complex may be made up into a solution or suspension in a suitable sterile aqueous or non-aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The complex may be administered intranasally or by inhalation including, but not limited to, an intranasal spray or by pulmonary inhalation with an appropriate carrier Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form. Typically, 5-25 mg of drug per day are administered.

Also included herein are methods of treating a neurological disease in a subject in need thereof by administering the complexes described herein. Exemplary neurological diseases include Alzheimer's Disease, Parkinsons' Disease, Myasthenia gravis, or Amyotrohic lateral sclerosis, specifically Alzheimer's Disease.

The invention is further illustrated by the following non-limiting examples.

Example 1: Computational Design of Amyloid Peptides Binding to the AD Drugs

Input information: Selection of an Amyloid Designable Scaffold, Structural Analysis and Determination of its Mutable Positions. Uncovering How Amino Acid Motifs Bind to Donepezil, Tacrine, Galantamine, and Memantine According to Experimentally Resolved Protein Structures in the PDB.

It was recently shown by Kokotidou et al (FEBS Lett. 2018; 592(1 1): 1777-1788) that the peptide with sequence YATGAIIGNII (SEQ ID NO: 7) self-assembles into amyloid fibrils which can be considered amyloid designable scaffolds due to the fact that the first three and last two residues are primarily not involved in β-sheets. According to computational predictions, the peptide can self-assemble into both antiparallel and parallel β-sheet conformations, with a higher propensity toward antiparallel β-sheet conformations. Both the first three and last two residues are sufficiently solvent exposed outside the key β-sheet core comprising residues GAIIG (SEQ ID NO: 1), and thus the terminal positions can be considered mutable positions to yield a specific functionality. The top fifty most highly-ordered and well-aligned antiparallel and parallel β-sheet conformations formed by the peptide were used independently as flexible structural templates in the optimization-based design, and the first and last two residue positions were considered as mutable, aiming to achieve binding to the four AD drugs under investigation. The flexible structural templates were represented by an elementary β-sheet structural unit comprising four β-sheet bonded peptides.

Experimentally resolved structures of proteins in complex with any of the AD drugs, e.g. donepezil, tacrine, galantamine, and memantine, were collected, along with their Protein Data Bank (PDB) IDs from the PDB (Nucleic Acids Res. 2019; 47(D1):D464-D474). From the collected protein structures, primary and secondary materialphore models (as defined in a previous computational study by Jonnalagadda et al (J Phys Chem B. 2018; 122(30):7555-7568) on the design of amyloid peptides binding to cesium ions) were extracted for each of the four AD drugs independently, mapping the geometries of amino acids interacting with the four compounds independently, in experimentally resolved protein structures. Within a binding pocket of a compound interacting with amino acids in a specific PDB structures, primary materialphore models represent the all possible relative distances of pairs of interacting amino acids, and secondary materialphore models represent all distances between the amino acids and the center of mass of the compounds. Amino acids and compounds in the aforementioned definitions are geometrically described by their centers of mass, and an amino acid is considered to be within a compound's binding pocket if their distance is below 8.5 Å.

The analysis resulted in the extraction of multiple materialphore models for each of the four AD drugs. Given the fact that, in each experimentally resolved structure, a certain compound may have been resolved to bind to multiple either nearly identical or diverse binding pockets, the total number of materialphore models extracted for each compound is equal to the sum of the number of experimentally resolved proteins multiplied by the number of complexed compounds with each proteins. Nearly identical binding pockets were automatically considered individually to avoid exclusion of any possible binding mode, as this would not add to the complexity of solving the optimization-based model design model, described below, due to limited number of materialphore models that could be extracted (as the number of experimentally resolved structures of proteins complexed with the compounds is low).

In the present study, the number of designable residue positions was selected to be equal to two per peptide per binding pocket, and thus upon β-sheet formation, the total number of residue positions amenable for subsequent design in each binding pocket is four. Since the primary and secondary materialphore models can contain more than four amino acids interacting with the compounds (as the number of amino acids interacting with the compound can be greater than four), "slices" of materialphore models were used for subsequent design purposes. For a given materialphore model, the slices represent combinations of four amino acids interacting with the compounds, and are used as input information in the optimization-based design. Constraints introduced in the optimization-based model can reduce the number of possible combinations that can be considered feasible during design. Primary materialphore models were used as input in the optimization-based design model, and contain all information needed for the design of the amyloid scaffold's mutable residue positions so that the newly placed amino acids can geometrically mimic how amino acids bind to a compound of interest (e.g., donepezil, tacrine, galantamine, and memantine) according to experimentally resolved structures in PDB. Both primary and secondary materialphore models were used to examine if the designed peptides' elementary β-sheet structural units can within the simulations form binding pockets resembling the corresponding materialphore model they were derived from (see below).

Optimization-Based Design of Functional Amyloid Materials Aiming to Bind to Donepezil, Tacrine, Galantamine, and Memantine. An optimization-based model was recently developed in a previous computational study by Jonnalagadda et al (J Phys Chem B. 2018; 122(30):7555-7568) with the capacity to introduce mutations at non-β-sheet residue positions of an amyloid designable scaffold in such a way that they mimic how amino acids bind to particular ions/compounds of interest according to experimentally resolved structures (represented by primary materialphore models), and aiming at energetically stabilizing the bound conformation of the pockets. The former is accomplished through constraints matching the relative distances between amino acids in (slices of) materialphore model with the corresponding relative distances of the introduced amino acids on the amyloid designable scaffold, while the latter is taken into account through energy minimization of the substituted amino acids in a coarse-grained energy representation, originating from values derived within the SIPPER force field (Pons et al, J Chem Inf Model. 201 1; 51(2):370-7) in the objective function of the model. In this study the optimization-based design model has been further advanced and implemented for the design of amyloid materials binding to the four AD drugs of interest.

Since the optimization-based design model was solved for both antiparallel and parallel flexible structural templates of the amyloid designable scaffold for all four compounds, eight optimization-based model problems were solved using exhaustive enumeration, independently. Out of the $20^4$ (20: total number of natural amino acids, 4=2±2: number of mutable positions per peptide) theoretical number of possible designed peptides, the optimization model produced 644, 7841, 1899, and 1703 different designed peptides that could potentially bind to donepezil, tacrine, galantamine, and memantine respectively on antiparallel flexible structural templates, as well as 18, 1258, 165, and 420 different designed peptides that could potentially bind the drugs on parallel flexible structural templates. The total number of designed peptides (originating from antiparallel and parallel flexible structural templates) is lower for donepezil because it has the lowest number of materialphore models.

Upon solution of the eight problems, peptide sequences were selected which could potentially bind to all four AD drugs under investigation, and thus the sequences which were common across all the four AD drugs were identified. Furthermore, an additional constraint was introduced to identify designed peptide sequences which could be functional in both antiparallel and parallel configurations. The aim was to improve the success rates as the finally produced designed materials which could potentially be functional irrespective of the dominant configuration adopted by each peptide. The introduction of the additional selection feature and constraint yielded a limited number of three solutions, FYTGAIIGNYF (SEQ ID NO: 3), YFTGAIIGNFY (SEQ ID NO: 4), and YFTGAIIGNYF (SEQ ID NO: 5), which were common across all the eight set of design and possessed lowest energies as estimated within the objective function. The two lowest in energy (FYTGAIIGNYF (SEQ ID NO: 3) and YFTGAIIGNFY (SEQ ID NO: 4)), defined by the minimized term in the objective function) were selected for further investigation comprising simulations, structural and energetic analyses, which evaluated the capacity of the two peptides to self-assemble into highly ordered and well-aligned β-sheets and form binding pockets which possess the expected geometry (in line with the materialphore models they were derived from) to bind to the compounds in the absence or presence of the compounds. FIG. 1*a* illustrates the chemical structure of YFTGAIIGNFY (SEQ ID NO: 4). The compounds' ability to be inserted in the designed binding pocket and their affinity to bind to the designed peptides' elementary β-sheet structural units was also studied.

MD Simulations Investigating the Self-assembly Properties of the Designed Peptides and Computational Validation Against the Primary and Secondary Materialphore Models. Three independent REMD simulation runs were performed in CHARMM (Brooks et al, J Comput Chem. 2009; 30(10): 1545-614) to investigate each of the two peptides' self-assembly structural properties, which were analyzed according to a protocol developed in previous studies (Tamamis et al, Methods Mol Biol. 2014; 1216:53-70). The simulation runs were performed for each of the two peptides independently in triplicates in order to increase the statistical sampling of β-sheet conformations used in our analysis. The propensities of β-sheet conformations were analyzed and the statistical convergence of the highly populated β-sheet conformations was verified as a function of time. Within the simulations, YFTGAIIGNFY (SEQ ID NO: 4) acquired an overall higher tendency for antiparallel compared to parallel configurations, whereas the designed peptide FYTGAIIGNYF (SEQ ID NO: 3) acquired a dominant tendency for parallel configurations. Subsequently, the top 500 highly ordered and well-aligned 4-stranded β-sheet conformations of the two peptides in their most dominant configuration were extracted, antiparallel for YFTGAIIGNFY (SEQ ID NO: 4) and parallel for FYTGAIIGNYF (SEQ ID NO: 3). First, the propensities of β-bridge formation between per pairs of residues in the β-sheets were analyzed, which showed that the designed amino acids were predominantly not involved in β-sheets. The calculated propensities of the two peptides were highly similar to the corresponding propensities of YATGAIINII (SEQ ID NO: 6) which served as the amyloid designable scaffold they were derived from, while the main difference between the two is associated with the fact that Phe2 and Thr3 in the designed peptide YFTGAIIGNFY (SEQ ID NO: 4) can be involved in the β-sheets to a small extent. Subsequently, a two-component computational validation procedure was performed, as in the study of Jonnalagadda et al (J Phys Chem B. 2018; 122(30):7555-7568), comparing the geometries of the binding pockets formed by the designed amino acids, in comparison to their corresponding geometries in the primary and secondary materialphore models, derived from experimentally resolved structures.

Within the comparative analysis, primary and secondary matches were identified. The former denotes the potential capacity of the designed amino acids in the two peptides to form binding pockets such that the distances between their centers of mass in the extracted β-sheet conformations are similar to the corresponding distances of the same amino acids within the primary materialphore models from which the designed peptides originated. If a primary match occurs, then the secondary match denotes the capacity of the designed amino acids in the two peptides to form binding pockets such that the distances between their centers of mass and the hypothetical center of mass of the four compounds are similar to the corresponding distances between the same amino acids and the compounds within the secondary materialphore models. The percentage values for the first and second validation components corresponding to the two matches were relatively high, an indication that even in the absence of compounds, the two peptides can adopt proper binding pockets at which the designed amino acids belonging to two adjacent β-sheet bonded peptides can form binding pockets resembling the experimentally resolved ones they originated from. Docking studies were performed in the following section to assess the structure and binding free energy of the four AD drugs to bind to the designed amino acid pockets within the two-peptides' β-sheet conformations.

Docking Studies Investigating the Structure and Binding Free-Energy of the Four AD Drugs to the Designed Amyloid Peptides. Docking of the AD drugs to the binding pockets of the two designed peptides with primary and secondary materialphore model matches was performed to assess the compounds': (1) ability to be inserted in the designed binding pocket and to be oriented such that they interact with the designed amino acids, in line with their corresponding interactions to the amino acids within the PDB structures they were derived from, and (2) binding free energy, by evaluating their energetic favorability to bind to the two designed peptides' extracted β-sheet structures, represented by their elementary β-sheet structural units. Instead of using available standard docking algorithms which could possibly randomly place each of the four compounds in complex with the β-sheet structures formed by the two peptides (within or without the binding pocket composed of the designed amino acids), without any guidance on the key expected interactions between them and the designed amino acids, we developed in-house docking programs written and executed in CHARMM (Brooks et al, J Comput Chem. 2009; 30(10): 1545-614). The in-house programs used a manually-constrained docking procedure which aimed to provide the designed amino acids with the ability to adjust in the presence the compounds, as well as accommodate the compounds similarly to how the same amino acids bind to the compounds in the corresponding experimentally resolved structures that each design originated from, aiming to mimic the naturally occurring process. For this purpose, the definitions of the previously defined materialphore models were expanded to additionally include tertiary and quaternary materialphore models, entailing for each corresponding (slice of a) materialphore model key additional information on distances corresponding to any type of potential electrostatic, hydrogen-bond, cation-π, π-π, hydrophobic-π or simply hydrophobic interactions between the amino acids and the compounds. The distances of these interactions included in the tertiary and quaternary materialphore models were prioritized according to their importance and were used as constraints during energy minimization which allowed docking and refinement of interactions of the four compounds to the designed amino acids within both peptides' 4-stranded β-sheet structures.

At the end the minimization-based docking procedure which resulted in the docking of the molecules into the designed peptides' binding pockets, the final potential energy of the constraint terms was recorded, and was used as a first metric to ensure that within the docked output structure, a sufficiently high level of mimicry was achieved; docked structures accompanied by a constraint energy above a certain cutoff were discarded and considered as infeasible solutions. The cutoff value was used to ensure that imposed distance constraints within the tertiary and quaternary materialphore models were met to a sufficiently reasonable extent for the structures chosen to be analyzed in the last step of energy computations. At the last step a slight additional energy minimization of 50 steps was introduced in CFLARMM, and the final output structure was extracted to evaluate the compounds' binding free energy using AutoDock Vina Scoring function (Trott and Olson, J Comput Chem. 2010; 3 1(2):455-61). Finally, we introduced, a second metric, an a posteriori criterion to ensure that after minimization, the minimum distance between a designed amino acid and a heavy atom of a compound does not exceed 6 Å, which constitutes an additional check to verify the participation of all designed amino acids in the binding. Also, calculations were performed in such a way that non-designed amino acid side chains (e.g., which are part of the amyloid scaffold) may also contribute to the binding free energy in addition to the designed amino acid side chains.

The above docking procedure served as an ultimate test to select computationally predicted docked structures that had already been validated by primary and secondary matches, for their ability to form the proper binding pockets so that the compounds can bind to the designed amino acids similarly to how they bind to amino acids within the experimentally resolved structures. Specifically, the first metric defined by the final potential energy of the constraint terms calculated above for each docked structure indicated to which extent the mimicry could be achieved. The binding free energies estimated between the docked compounds and the designed peptides enabled us to estimate the binding free energy of each of the four compounds to the designed amyloid materials (represented computationally by their elementary structural β-sheet units), enabling us to investigate the relative tendency of the four compounds to bind to the designed amyloid peptides. Nevertheless, the constraints in the first metric were not fully met, and thus the degree of mimicry between the geometry of the designed amino acids and the materialphore model they originated from was considered acceptable, but not necessarily perfect.

Upon computational docking the four AD drugs to the extracted β-sheet structures of both YFTGAIIGNFY (SEQ ID NO: 4) and F YT GAIIGNYF (SEQ ID NO: 3), the top ten binding modes with the highest affinity (i.e., lowest binding free energy assessed with Autodock Vina's scoring function (Trott O, Olson A J, J Comput Chem. 2010; 3 1(2):455-61) were selected for both designed peptides. Any docked conformations failing to reproduce the constraints imposed by the tertiary or quaternary materialphore models were not considered in the selection. The selection of the top ten binding modes was based on the observation that overall the lowest free energy modes of each of the four AD drugs in complex with the two peptides correspond to binding modes with not necessarily very high structural similarity, but with alike interactions and similar molecular recognition properties. The presence of alike interactions rather than identical across different binding modes is attributed to the variability of the designed amino acids' geometries in the β-sheet structures used for docking. Due to the variability, the distances of interactions within the binding modes were not necessarily identical to the imposed distance constraints within the tertiary and quaternary materialphore models. Importantly, the energy minimization used in the presence of constraints allowed the compounds to optimize their interactions with the designed amino acids according to the materialphore models.

Subsequently, a statistical analysis of the binding free energies of the four AD drugs in complex with the two peptides' β-sheet structures was performed. FIG. 1B and FIG. 1c represent the computationally predicted binding free energies for (D) donepezil, (T) tacrine, (G) galantamine, and (M) memantine in complex with the designed peptides YFTGAIIGNFY (SEQ ID NO: 4) and FYTGAIIGNYF (SEQ ID NO: 3). The results suggest that donepezil and tacrine have relatively higher affinity for the two designed peptides, YFTGAIIGNFY (SEQ ID NO: 4) and F YT GAIIGNYF (SEQ ID NO: 3), than galantamine and memantine. To confirm that the trend (observed in FIG. 1) is not an artifact of the fact that the statistical analysis was performed on the top 10 structures, we expanded our analysis to top 25 and top 50 structures, independently, and observed the same trend. It is worth noting that the computational predicted binding free energies could be interpreted as a means to suggest a trend of energetic favorability of the designed peptides to the four AD drugs, rather than the ability of a designed peptide to bind to a compound or not. The relatively low free energies suggest that the two designed peptides have tendency to bind to all four compounds, achieving our original goal, while the binding free energy to Donepezil and Tacrine is predicted to be lower (and more energetically favorable) than Galantamine and Memantine.

FIGS. 2 and 3 present two of the docked AD drugs binding to the four designed (two initial and two terminal) amino acids in the β-sheet structures of the two amyloid peptides.

A visual inspection of the computationally predicted interactions formed by the four AD drugs in complex with the two designed amino acids of the extracted β-sheets of the two designed peptides was performed, following the docking procedure. Donepezil primarily adheres to the binding pocket formed by the four designed amino acids of the two peptides. In the case of the YFTGAIIGNFY (SEQ ID NO: 4) peptide, Donepezil adheres to the designed binding pocket primarily through its amine containing moiety (FIG. 2a), while in the FYTGAIIGNYF (SEQ ID NO: 3), the entire compound adheres to the binding pocket formed by the four designed amino acids (FIG. 2b). For both designed peptides, Donepezil forms rich π-π and cation-π interactions with designed amino acids (FIGS. 2a and 2b). Additionally, for both the designed peptides, the amine group of donepezil forms a hydrogen bond with the hydroxyl group of the designed tyrosines of the elementary β-sheet structural units formed by both peptides in nearly half of the top ten selected structures.

Tacrine is primarily "wrapped" by the designed amino acids of the YFTGAIIGNFY (SEQ ID NO: 4) peptide, which cluster around the entire compound (FIG. 3 a), whereas it primarily adheres to the binding pocket formed by the four designed amino acids of the FYTGAIIGNYF (SEQ ID NO: 3) peptide (FIG. 3b). For both designed peptides, Tacrine forms rich π-π and cation-π interactions with the designed amino acids (FIGS. 3 a and 3b), and additionally forms a hydrogen bond with the hydroxyl group of the designed tyrosines through both its charged and uncharged amine groups of the respective designed peptides in nearly half of the top ten selected structures.

Similarly, in data not shown, the central core of galantamine is primarily "wrapped" by the designed amino acids of the YFTGAIIGNFY (SEQ ID NO: 4) peptide, whereas it primarily adheres to the binding groove formed by the designed amino acids in the case of FYTGAIIGNYF (SEQ ID NO: 3). For both designed peptides, galantamine forms rich πx-π and cation-π interactions with the designed amino acids. For the designed peptide YFTGAIIGNFY (SEQ ID NO: 4), galantamine forms a hydrogen bond with the hydroxyl group of the designed tyrosines through its charged amine group in nearly half of the top ten selected structures, as well as through its hydroxyl group in three of the top ten selected structures. For the designed peptide FYTGAIIGNYF (SEQ ID NO: 3), galantamine forms a hydrogen bond with the hydroxyl group of the designed tyrosines through its charged amine group in three of the top ten selected structures, as well as through its hydroxyl group in two of the top ten selected structures.

In data not shown, memantine is primarily loosely-"wrapped" by the designed amino acids of both designed peptides YFTGAIIGNFY (SEQ ID NO: 4) and FYTGAIIGNYF (SEQ ID NO: 3), which cluster around the entire compound. Memantine is not tightly"wrapped", as is the case of Tacrine, presumably due to the bulkier shape of Memantine. For both designed peptides, Memantine forms rich hydrophobic-p and cation-p interactions with the designed amino acids. Additionally, for both designed peptides, Memantine forms hydrogen bonds with the hydroxyl group of the designed tyrosines through its amine group in nearly half of the top ten selected structures for each of the designed peptides.

Methods: Studies of Designed Amyloid Peptides in Solution

Amyloid Peptide/Inhibitor Coordination Studies in Dilute Solutions. Amyloid peptide carrier (YFTGAIIGNFY (SEQ ID NO: 4) and FYTGAIIGNYF (SEQ ID NO: 3) dispersions containing inhibitors were prepared at 1 mg/mL by addition of 1 mL of 150 µM inhibitor (donepezil, tacrine, galantamine, memantine) solution prepared in 0.1 M PBS buffer (pH=7.4) into 1 mg peptide. As a negative control, 1 mL of 0.1 M PBS buffer was added. The mixtures were vortexed and sonicated to homogenously disperse any solid aggregates and stirred overnight to allow for coordination. The mixtures were transferred to 2 mL Eppendorf tubes and centrifuged for 15 mins at 4,400 rpm (14° C.) to pelletize the amyloid bound-inhibitors, and the supernatant was decanted. Subsequently, 1 mL of DI water was added to wash the pellet (followed by vortexing until obtaining a homogenous dispersion) in order to remove any unbound inhibitor. The samples were then centrifuged again at the same conditions so as to pelletize the amyloid materials, and the supernatant was decanted. Another 1 mL of DI water was then added into the pellet, the mixture was vortexed, and the physically bound inhibitor into the dilute amyloid peptide dispersions was quantified by UV-Vis between 200-600 nm and MS. This step is denoted as wash 1 in our study. Two additional pellet purification cycles were realized with replacement of the decanted volume each time with 1 mL of fresh DI water (denoted as wash 2 and wash 3 respectively). The inhibitor-containing peptides amyloids were normalized at 400 nm over the respective no inhibitor-containing amyloid peptides at the specific washing step, and the measured inhibitor peak values (at 315 nm and 323 nm) were subtracted from that of the amyloid peptide carriers at the same wavelength and concentration. The amount of inhibitors coordinated with the amyloid peptide carriers was quantified based on a calibration curve by both UV-Vis and MS.

DonepeziPHCl shows three peaks in the UV-Vis spectrum at 230, 271, and 315 nm and has a lower molar absorptivity than Tacrine. The peak at 315 nm was selected for inhibitor quantification due the absence of peaks at that range for both peptides. Results showed a slightly shifted peak for both amyloid peptides/Donepezil to 316 nm. However, the peak at 315 nm was selected for inhibitor quantification, and the following equation was used for both peptides:

$$A_{315} = A_{315\ (YFTGAIIGNFY/Donepezil)} - A_{315\ (YFTGAIIGNFY)}$$

Tacrine*HCl shows three peaks, as well, in the UV-Vis spectrum at 240, 323, and 336 nm. The peak at 323 nm was used for inhibitor quantification due the absence of peaks at that range for both peptides. Results, similarly to Donepezil, showed a slightly shifted peak for both amyloid peptides/tacrine at 325 nm. However, the peak at 323 nm was selected for inhibitor quantification, and the following equation was used:

$$A_{323} = A_{323\ (FYTGAIIGNYF/Tacrine)} - A_{323\ (FYTGAIIGNYF)}$$

Amyloid Fibrils Preparation and Characterization. For the formation of fibrils, the amyloid peptides were dispersed in DI water at a 10 mg/ml, vortexed, heated at 60° C. for 30 sec, and sonicated for 15 mins (this cycle was repeated 10 times overall), and finally left overnight at room temperature to form a hydrogel. Both peptides showed initially an increase in viscosity, while increased blurriness was observed by time, denoting fibril formation. That was confirmed with Field Emission Scanning Electron Microscopy (FESEM) and Congo Red staining (CR).

Coordination Studies at Higher Peptide Concentrations and Inhibitor Capturing. A 1 mL inhibitor solution (donepezil, tacrine, galantamine, memantine) at 1000 M in 0.1 M PBS buffer (pH=7.4) was added in the YFTGAIIGNFY (SEQ ID NO: 4) or FYTGAIIGNYF (SEQ ID NO: 3) amyloid peptide gels (10 mg/mL, 1 mL volume) and was left to physically complex under stirring overnight (the final peptide concentration was diluted to 5 mg/mL). A control using 1 mL of 0.1 M PBS (no inhibitor) was also prepared. The complexed amyloid/inhibitor materials were then transferred to 5 mL conical Eppendorf tubes, and centrifuged for 15 mins at 4,400 rpm (14° C.). The supernatant was decanted, and 2 mL of DI water were subsequently added to wash the pellet (followed by vortexing until obtaining a homogenous dispersion) in order to remove any unbound inhibitor. The samples were then centrifuged again at the same conditions so as to pelletize the amyloid materials, and the supernatant was decanted. Another 2 mL of DI water were then added into the pellet, the mixture was vortexed, and the physically bound inhibitor into the amyloid peptides was quantified by UV-Vis between 200-600 nm and MS. This step is denoted as wash 1 in our study. Two additional pellet purification cycles were realized with replacement of the decanted volume each time with 2 mL of fresh DI water (denoted as wash 2 and wash 3 respectively). The inhibitor-containing amyloid peptides were normalized at 400 nm over the respective no inhibitor-containing ones at the specific washing step. The measured values of inhibitor peaks (315 nm for donepezil or 323 nm for tacrine) were subtracted from that of the amyloid peptide carriers at the same concentration.

Incubation of Amyloid Gels-Containing Inhibitors in PBS at 37° C. YFTGAIIGNFY (SEQ ID NO: 4) amyloid gels were prepared at 10 mg/mL (1 mL) and a 0.1 M PBS solution of Donepezil was added at 1000 µM (1 mL) and was left to stir overnight (the final peptide concentration was diluted to 5 mg/mL). A control of 1 mL 0.1 M PBS was also prepared. The complexed amyloid/inhibitor was sequentially centrifuged, and the same volume of water (2 mL) was added in the pellet to wash it (followed by vortexing until obtaining a complete dispersion) and remove the unbound inhibitor (wash 1). The sample was centrifuged, the pellet was isolated, and 2 mL of 0.1 M PBS was added, followed by overnight incubation under stirring at 37° C. The inhibitor-containing peptide was then pelletized, the supernatant was decanted, and the peptide/inhibitor dispersion was quantified after addition of 2 mL water (wash 2). A second washing step with 2 mL fresh water was subsequently realized and the pellet was quantified again (wash 3).

Example 2: Coordination of the Designed Amyloid Peptides with AD drugs in Dilute Solution.

The two computationally-designed amyloid materials FYTGAIIGNYF (SEQ ID NO: 3) and YFTGAIIGNFY (SEQ ID NO: 4) were sequentially tested experimentally for possible coordination with the four AD drugs in dilute solutions, as well as at higher peptide concentrations, examining further the impact of inhibitor binding. From all the marketed AD drugs, donepezil and tacrine are known to induce the highest inhibition towards AChE (following the Ellman's assay), galantamine shows moderate inhibition, while memantine (NMDA receptor antagonist) has negligible inhibition towards AChE. Donepezil, galantamine, rivastigmine, and memantine are the only FDA-approved drugs for AD, where the first three act as cholinesterase inhibitors, and regulate the levels of the neurotransmitter acetylcholine, while memantine is an NMDA receptor antagonist that regulates the levels of glutamate (another neurotransmitter). On the other hand, tacrine, the first AD approved drug historically (though it has been removed from the market), has been used widely as a model AChE inhibitor for enzyme deactivation and crystallographic studies.

Both the computationally designed amyloid peptides FYTGAIIGNYF (SEQ ID NO: 3) and YFTGAIIGNFY (SEQ ID NO: 4) showed ability to coordinate with AD drugs, in agreement with the computational studies, in both dilute peptide concentration (FIGS. 4 and 5) and at higher peptide concertation (FIG. 6). Binding of the designed amyloid materials to donepezil and tacrine was confirmed by both UV-Vis and mass spectroscopy (MS) (FIGS. 4-6) after pelletizing the material and purifying it from unbound inhibitors, while for galantamine and memantine, MS was only used, due to an overlapping peak in the UV-Vis of galantamine with the amyloid peptide carrier (peaks at 278 and 285 nm due to benzene rings of tyrosine and phenylalanine), and the absence of any chromophore in the case of memantine (data not shown).

Figure 4:
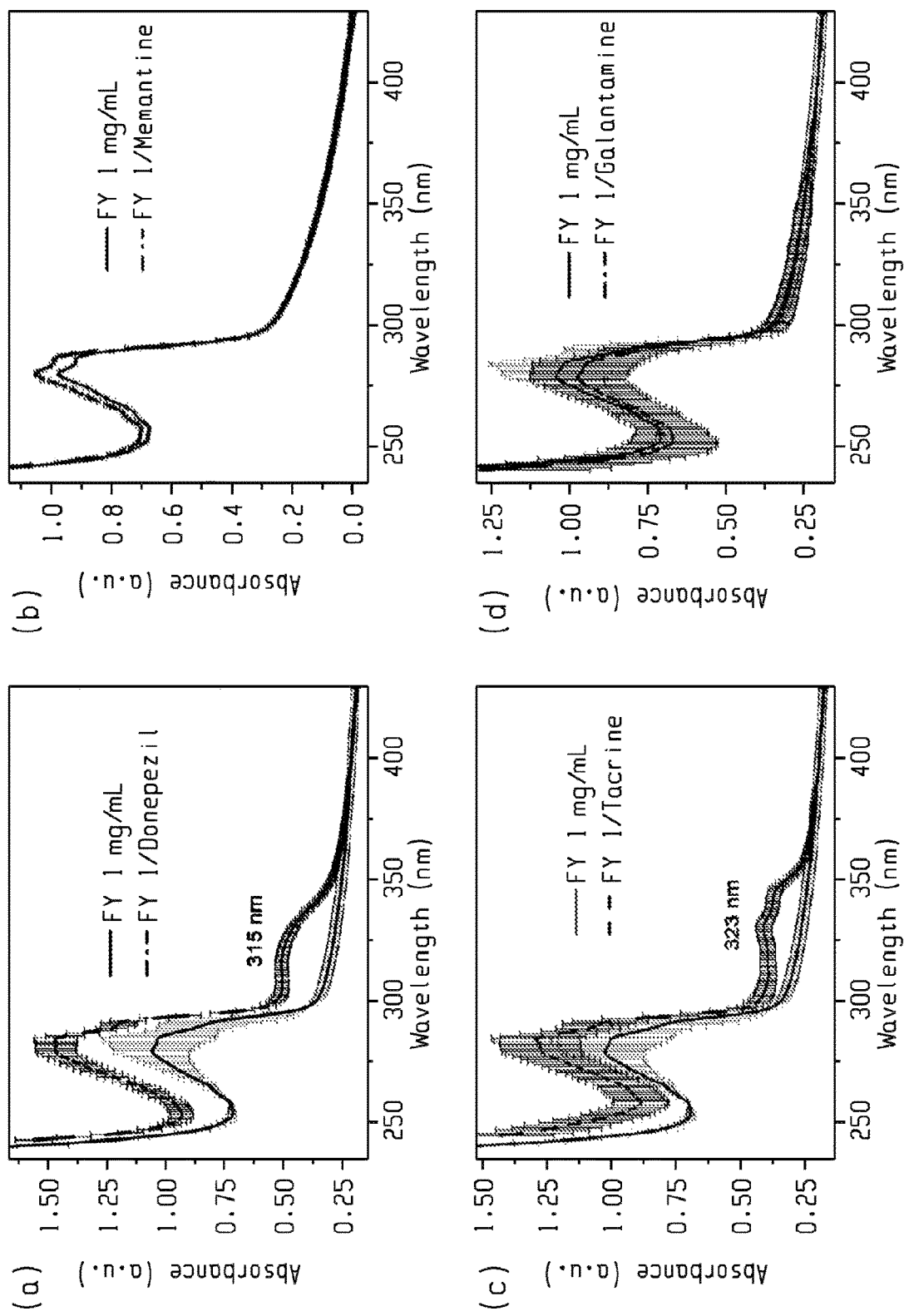
FIGS. 4a-d show UV-Vis spectra of FYTGAIIGNYF (SEQ ID NO: 3) at 1 mg/mL showing coordination of FIG. 4a donepezil and FIG. 4c tacrine compared to the free amyloid peptide carrier (FY1), unlike FIG. 4b memantine and FIG. 4d galantamine where no peaks are shown. Drug quantification was performed using the peak of donepezil at 315 nm and that of tacrine at 323 nm respectively.

UV-Vis results showed incorporation of 26 µM tacrine and 38 µM donepezil (out of the 150 µM loaded) into the YFTGAIIGNFY (SEQ ID NO: 4) peptide (approximately ⅕ and approximately ¼ respectively), while 21 µM tacrine and 33 µM donepezil were incorporated into the FYTGAIIGNYF (SEQ ID NO: 3) peptide (approximately ⅐ and approximately ⅕ respectively), after removing the supernatant and washing the pellet (first wash), as shown in FIG. 4. To highlight the strong physical interactions and inhibitor capturing by the amyloid carriers, several pellet washing steps were realized, reassuring that the inhibitor peaks were only due to physical binding. The YFTGAIIGNFY (SEQ ID NO: 4) peptide at 1 mg/mL (abbreviated as YF1) showed capturing of 38±4 µM ($1^{st}$ pellet wash), 24±4 µM ($2^{nd}$ pellet wash), and 5±4 µM ($3^{d}$ pellet wash) of Donepezil, as well as 26±2 µM ($1^{st}$ pellet wash), 14±2 µM ($2^{nd}$ pellet wash), and 3±2 µM ($3^{d}$ pellet wash) of Tacrine (Table 1). The FYTGAIIGNYF (SEQ ID NO: 3) peptide at 1 mg/mL (abbreviated as FY1), on the other hand, showed 33±4 µM ($1^{st}$ pellet wash), 28±5 µM ($2^{nd}$ pellet wash), and 20±5 µM ($3^{d}$ pellet wash) of Donepezil, as well as 21±4 µM (1st pellet wash), 17±4 µM (2"d pellet wash), and 13±3 µM ($3^{a}$ pellet wash) of tacrine (Table 1). Both results overall indicated slightly higher capturing of inhibitor at the initial stage for the YFTGAIIGNFY (SEQ ID NO: 4) peptide at 1 mg/mL, but with higher capturing efficiency for the FYTGAIIGNYF (SEQ ID NO: 3) peptide at subsequent washings.

Galantamine and memantine were quantified by MS, and thus the same technique was also for donepezil and tacrine for comparison. Results showed higher coordination for memantine with the FYTGAIIGNYF (SEQ ID NO: 3) peptide compared to YFTGAIIGNFY (SEQ ID NO: 4) at 1 mg/mL (18±3 vs. 8±1 µM; $1^{st}$ pellet wash), while galantamine seemed to coordinate equally with both peptides, though at a low rate (3±2 vs. 4±1 µM; $1^{st}$ pellet wash), as shown in Table 1 and FIG. 5. The slightly higher memantine coordination for YTGAIIGNYF (SEQ ID NO: 3) compared with YFTGAIIGNFY (SEQ ID NO: 4) was also followed at subsequent washings, with 5±2 vs. 3±1 µM ($2^{nd}$ pellet wash), and 4±2 vs. 2±1 µM ($3^{d}$ pellet wash). On the other hand, galantamine showed negligible coordination with both peptides after subsequent washings, suggesting weak interaction (Table 1).

Donepezil and tacrine capturing by both peptides was also examined by MS. Results showed coordination of 29±4, 24±8, and 23±6 µM for tacrine for the FYTGAIIGNYF (SEQ ID NO: 3) peptide at the $1^{st}$, $2^{nd}$, and $3^{d}$ washings, compared with 37±2, 2±2, and 0 µM obtained for the YFTGAIIGNFY (SEQ ID NO: 4) at 1 mg/mL (Table 1 and FIG. 5). The YF1 peptide seemed to initially coordinate a higher amount of tacrine, compared to the F Y 1 peptide, but that interaction did not seem to be strong enough to keep the drug bound at subsequent washings. Additionally, donepezil showed coordination of 51±3, 47±0, and 43±4 µM in the FYTGAIIGNYF (SEQ ID NO: 3) peptide at the $1^{st}$, $2^{nd}$, and $3^{d}$ washings, compared with 43±6, 32±4, and 21±9 µM obtained for the YFTGAIIGNFY (SEQ ID NO: 4) at 1 mg/mL (Table 1). Thus, the FY1 peptide seemed to bind stronger to donepezil and tacrine compared to the YF1 (FIG. 5). The slightly higher amount of inhibitors found coordinated for both peptides by MS compared to UV-Vis is maybe due to the higher solubility of both inhibitors and the peptide in methanol compared to water.

Table 1. Quantification of Ad Compounds Captured by the Amyloid Peptides at 1 Mg/Ml

TABLE 1

QUANTIFICATION OF AD COMPOUNDS CAPTURED BY THE AMYLOID PEPTIDES AT 1 MG/ML

| Sample | Wash 1# (µM) | Wash 2# (µM) | Wash 3# (µM) | Wash 1* (µM) | Wash 2* (µM) | Wash 3* (µM) |
|---|---|---|---|---|---|---|
| FY10-Don.150 | 33 ± 4 | 28 ± 5 | 20 ± 5 | 51 ± 3 | 47 ± 0 | 43 ± 4 |
| FY1-Tac.150 | 21 ± 4 | 17 ± 4 | 13 ± 3 | 29 ± 4 | 24 ± 8 | 23 ± 6 |
| FY1-Mem.150 | — | — | — | 18 ± 3 | 5 ± 2 | 4 ± 2 |
| FY1-Gal.150 | — | — | — | 3 ± 2 | 0 | 0 |
| YF1-Don.150 | 38 ± 4 | 24 ± 4 | 5 ± 4 | 43 ± 6 | 32 ± 4 | 21 ± 9 |
| YF1-Tac.150 | 26 ± 2 | 14 ± 2 | 3 ± 2 | 37 ± 2 | 2 ± 2 | 0 |
| YF1-Mem.150 | — | — | — | 8 ± 1 | 3 ± 1 | 2 ± 1 |
| YF1-Gal.150 | | | | 4 ± 1 | 0 | 0 |

By UV-Vis based on a calibration curve;
*By MS based on a calibration curve. The peptides were left to react overnight at 1 mg/mL with 150 µM inhibitor, and then pelletized to remove unbound inhibitor, followed by subsequent aqueous pellet washings (1-3).

Example 3: Experimental Verification of Amyloid Nature and Self-Assembly

In the second stage of this study, the ability of the designed peptides to form amyloid fibrils at higher peptide concentration was confirmed using field emission scanning electron microscopy (FESEM) and Congo Red (CR) staining. The amyloid peptides were shown to form distinctive fibrillar morphologies with widths in the range of 10-15 nm as observed under FESEM (data not shown). Additional investigation using CR staining confirmed the amyloid nature of the fibrils, showing green/yellow birefringence under polarized light, for both amyloids and amyloid peptide/D drugs complexes (data not shown). This clearly indicates that the complexed peptides can retain their amyloid nature while physically associating with AD drugs. Coupling these functional amyloid materials with AD drugs could allow for a high amount of inhibitors complexed with a physically associated network, permitting for high delivery of cargo (inhibitors) to the target enzyme.

Example 4: Coordination of the Designed Amyloid Peptides with AD Drugs at Higher Peptide Concentration The physical complexation at higher peptide concentration, yielding hydrogels, was examined post formation of both the amyloid gels at 10 mg/mL. The complexation of the AD compounds into amyloid gels was quantified by both UV-Vis and MS after overnight incubation to allow for complexation to occur (peptide concentration was reduced to 5 mg/mL), followed by centrifugation, and pellet formation (containing amyloid peptides/AD drugs), while the AD drug retention was also examined after subsequent pellet washings (Table 2 and FIG. 6). Both YFTGAIIGNFY (SEQ ID NO: 4) and FYTGAIIGNYF (SEQ ID NO: 3) (abbreviated as YF10 and FY10) amyloid fibrils showed ability to capture AD drugs at higher peptide concentration, even after extensive pellet washings, exhibiting high inhibitor retentions. UV-Vis results showed incorporation of 154±11 μM, 135±8 μM, and 117±5 UM of donepezil into the YFTGAIIGNFY (SEQ ID NO: 4) peptide at 5 mg/mL, after the $1^{st}$, $2^{nd}$ and $3^{d}$ pellet aqueous washings respectively, as well as 90±4 μM, 80±5 μM, and 73±5 μM of tacrine at the same concentration, after $1^{st}$, $2^{nd}$ and $3^{d}$ pellet washings (Table 2 and FIG. 6).

The FYTGAIIGNYF (SEQ ID NO: 3) peptide at 5 mg/mL showed incorporation of donepezil at 187±19 μM ($1^{st}$ pellet wash), 173±33 μM ($2^{nd}$ pellet wash), and 160±33 μM ($3^{d}$ pellet wash), as well as 104±16 μM ($1^{st}$ pellet wash), 82±9 μM ($2^{nd}$ pellet wash), and 72±10 μM ($3^{d}$ pellet wash) of tacrine (Table 2 and FIG. 6). While both peptides exhibited similar tacrine capturing efficiency (approximately 8%, relative to $2^{nd}$ pellet wash), the FYTGAIIGNYF (SEQ ID NO: 3) managed to capture a slightly higher amount of donepezil (17% vs 14%, relative to $2^{nd}$ pellet wash). This could be attributed to the higher water solubility of tacrine vs. donepezil, which could favor hydrophobic interactions for donepezil with the amyloid peptide. In addition, stronger affinity interactions of the benzyl groups of Donepezil with the initial and terminal exposed phenylalanines (F) in the FYTGAIIGNYF (SEQ ID NO: 3) peptide could possibly justify the slightly higher coordination compared to the YFTGAIIGNFY (SEQ ID NO: 4) peptide.

Table 2. Quantification of AD Compounds Captured by the Amyloid Peptides at 5 Mg/Ml (Table 2 and FIG. 6). The lower experimental capturing trend for galantamine was also predicted by the computational studies (FIG. 1). Donepezil and tacrine capturing was also examined by MS at higher peptide concentrations. Results showed coordination of 114±6, 102±2, and 94±10 UM for tacrine for the FYTGAIIGNYF (SEQ ID NO: 3) peptide at 5 mg/mL at the $1^{st}$, $2^{nd}$, and $3^{d}$ washings respectively. For the YFTGAIIGNFY(SEQ ID NO: 4) peptide, unlike the dilute peptide solutions where minimal amount of tacrine was found after subsequent washings, the amyloid fibril seemed to play a crucial role. Results showed coordination of 98±9, 75±4, and 63±8 μM after the $1^{st}$, $2^{nd}$, and $3^{d}$ washings respectively, highlighting the impact of fibril formation in coordination (Table 2 and FIG. 6). A similar trend was also observed for galantamine above (with negligible amount of inhibitor found for dilute solutions after subsequent washings). Donepezil showed the highest capturing potency (from all the inhibitors) at both peptides, with 163±4, 151±1, and 148±3 μM for the FYTGAIIGNYF (SEQ ID NO: 3) peptide at 5 mg/mL, as well as 154±7, 141±10, and 129±24 μM for the YFTGAIIGNFY (SEQ ID NO: 4) peptide. Similarly to tacrine, the FY10 peptide formed an amyloid fibril with a slightly higher capturing capacity compared to the YF10 one, based on both MS and UV-Vis.

A donepezil-coordinated amyloid peptide material was further examined after one day incubation at physiological conditions (37° C., PBS buffer) under stirring, to imitate in vivo circulating conditions. Donepezil seemed to be strongly bound to the YFTGAIIGNFY (SEQ ID NO: 4) peptide

TABLE 2

| Sample | QUANTIFICATION OF AD COMPOUNDS CAPTURED BY THE AMYLOID PEPTIDES AT 5 MG/ML | | | | | |
|---|---|---|---|---|---|---|
| | Wash 1[#] (μM) | Wash 2[#] (μM) | Wash 3[#] (μM) | Wash 1* (μM) | Wash 2* (μM) | Wash 3* (μM) |
| FY10-Don.1000 | 187 ± 19 | 173 ± 33 | 160 ± 33 | 163 ± 4 | 151 ± 1 | 148 ± 3 |
| FY10-Tac.1000 | 104 ± 16 | 82 ± 9 | 72 ± 10 | 114 ± 6 | 102 ± 2 | 94 ± 10 |
| FY10-Mem.1000 | — | — | — | 32 ± 2 | 16 ± 2 | 12 ± 3 |
| FY10-Gal.1000 | — | — | — | 22 ± 3 | 4 ± 2 | 3 ± 3 |
| YF10-Don.1000 | 154 ± 11 | 135 ± 8 | 117 ± 5 | 154 ± 7 | 141 ± 10 | 129 ± 24 |
| YF10-Tac.1000 | 90 ± 4 | 80 ± 5 | 73 ± 5 | 98 ± 9 | 75 ± 4 | 63 ± 8 |
| YF10-Mem.1000 | — | — | — | 21 ± 1 | 10 ± 1 | 8 ± 1 |
| YF10-Gal.1000 | — | — | — | 17 ± 1 | 4 ± 2 | 3 ± 2 |
| YF10-Don.1000 Inc.[§] | — | 121 ± 25 | 110 ± 31 | — | 128 ± 12 | 120 ± 18 |

[#]By UV-Vis based on a calibration curve.
*By MS based on a calibration curve. In formed at 10 mg/mL amyloid gels (top left image above), a 1000 μM inhibitor solution in PBS was added and left to react overnight (leading to 5 mg/mL). Samples were then pelletized to remove unbound inhibitor, followed by subsequent aqueous pellet washings (1-3) so as to examine the interaction strength of the bound inhibitor with the amyloid carrier (as shown in top right image).
[§]The amyloid peptide/inhibitor pellet, after a first aqueous wash to remove unbound inhibitors (1), was incubated at 37° C. in PBS for one day. Samples were then pelletized and quantified after two subsequent aqueous pellet washings (2-3).

The coordination of galantamine and memantine at higher peptide concentrations was quantified by MS, and the same quantification method was used for donepezil and tacrine for comparison. MS results confirmed higher coordination for memantine with the FYTGAIIGNYF (SEQ ID NO: 3) peptide compared to YFTGAIIGNFY (SEQ ID NO: 4) at 5 mg/mL (32±2 vs. 21±1 μM; $1^{st}$ pellet wash), while Galantamine showed a similar trend (22±3 vs. 17±1 μM; $1^{st}$ pellet wash), as shown in Table 2 and FIG. 6. The higher memantine coordination trend for FYTGAIIGNYF (SEQ ID NO: 3) compared with YFTGAIIGNFY (SEQ ID NO: 4) was also followed in subsequent washings, with 16±2 vs. 10±1 μM (2nd pellet wash), and 12±3 vs. 8±1 μM ($3^{d}$ pellet wash). On the other hand, galantamine showed a similar weak coordination for both peptides after subsequent washings, with 4±2 μM and 3±2 μM after the $2^{nd}$ and $3^{d}$ pellet wash respectively carrier, after incubation and subsequent washings, leading to similar results with those at room temperature. UV-Vis results showed incorporation of 121±25 μM and 110±31 μM of donepezil into the incubated YFTGAIIGNFY (SEQ ID NO: 4) peptide at 5 mg/mL after the $2^{nd}$ and $3^{a}$ pellet aqueous washings, values comparable with those at room temperature (135±8 μM and 117±5 μM respectively) (Table 2 and FIG. 6). A similar result was also confirmed by MS with 128±12 and 120±18 μM at the $2^{nd}$ and $3^{d}$ pellet aqueous washings for the incubated YFTGAIIGNFY (SEQ ID NO: 4) peptide, compared with 141±10 and 129±24 M for the one at room temperature (Table 2 and FIG. 6, denoting strong capturing.

The results overall indicate that the computationally designed functional amyloid biomaterials could be used as novel AD drug delivery carriers, motivated by their ability to experimentally capture efficiently inhibitors (AD drugs), binding to one or a combination of different AD drugs (cocktail), thereby driving the sustained release of AD drugs on target. This is, to our knowledge, the first study reporting functional amyloid materials capable of binding AD drugs. Both the computationally designed peptides manage to capture high amounts of tacrine and donepezil, as predicted, though slightly higher coordination is experimentally shown for the FYTGAIIGNYF (SEQ ID NO:3) peptide compared to YFTGAIIGNFY (SEQ ID NO: 4). In addition, the capturing of memantine using the same peptide scaffold is shown, though at lower amounts.

Among all cholinesterase inhibitors, donepezil and tacrine are the most effective towards in vitro AChE inhibition, and showed the highest capturing using our peptide carriers (FIG. 4-6). While tacrine was withdrawn from the market due to hepatotoxicity, donepezil has superior selectivity for AChE in the central nervous system. Recent studies showed the therapeutic efficacy of microneedles used for the delivery of donepezil, opening new avenues for similar cognition-enhanced injectable formulations. The computationally designed amyloid materials could serve as drug carriers binding to combinations of NMD A and cholinesterase inhibitors, as such have been shown to provide additional benefits to patients towards the monotherapy in moderate-to-severe AD. Thus, amyloid gels with complexed AD drugs could be either used in the gel form for transdermal drug release or via the nasal route (spraying), or they can be diluted and delivered orally.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A complex comprising an amyloid complexed with a cholinesterase inhibitor, an NMDA receptor antagonist, or a combination of a cholinesterase inhibitor and an NMDA receptor antagonist,
   wherein the amyloid peptide comprises $X_1X_2GAIIGX_3X_4$ (SEQ ID NO: 2), wherein
   $X_1$ and $X_4$ are each independently YF or FY, and $X_2$ and $X_3$ are each 1 amino acid long, and are each independently T, N, S, or Q; or $X_2$ and $X_3$ are each 2 amino acid long and $X_2$ is (Y or F)T, (Y or F)N, (Y or F)S or (Y or F)Q, and $X_3$ is T(Y or F), N(Y or F), S(Y or F) or Q(Y or F),
   wherein the amyloid peptide self-assembles into fibrils, and wherein the peptide has a total length of 11-13 amino acids.

2. The complex of claim 1, wherein the amyloid peptide comprises FYTGAIIGNYF (SEQ ID NO: 3), YFTGAIIGNFY (SEQ ID NO: 4), or YFTGAIIGNYF (SEQ ID NO: 5).

3. The complex of claim 1, wherein the cholinesterase inhibitor comprises donepezil, galantamine, rivastigmine, tacrine, neostigmine, or edrophonium.

4. The complex of claim 1, wherein the NMDA receptor antagonist comprises memantine, amantadine, ketamine, dizoclopine, or d-cycloserine.

5. A pharmaceutical composition comprising the complex of claim 1 and a pharmaceutically acceptable excipient.

6. The pharmaceutical composition of claim 5, in the form of a composition for oral administration, topical application, or intranasal administration.

7. A method of treating a neurodegenerative disease, comprising administering to a subject in need thereof the complex of claim 1.

8. The method of claim 7, wherein the neurodegenerative disease is Alzheimer's disease, Parkinsons' disease, Myasthenia gravis, or Amyotrohic lateral sclerosis.

9. The method of claim 7, wherein the neurodegenerative disease is Alzheimer's disease.

* * * * *

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: amyloidogenic core

<400> SEQUENCE: 1

Gly Ala Ile Ile Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: YF or FY
<220> FEATURE:
<221> NAME/KEY: VARIANT
<222> LOCATION: (2)..(2)
<223> OTHER INFORMATION: T, N, S, Q, (Y or F)T, (Y or F)N, (Y or F)S or
        (Y or F)Q
```

```
<220> FEATURE:
<221> NAME/KEY: VARIANT
<222> LOCATION: (8)..(8)
<223> OTHER INFORMATION: T, N, S, Q, T(Y or F), N(Y or F), S(Y or F) or
      Q(Y or F)
<220> FEATURE:
<221> NAME/KEY: VARIANT
<222> LOCATION: (9)..(9)
<223> OTHER INFORMATION: YF or FY

<400> SEQUENCE: 2

Xaa Xaa Gly Ala Ile Ile Gly Xaa Xaa
1               5

<210> SEQ ID NO 3
<211> LENGTH: 11
<212> TYPE: PRT
<213> ORGANISM: Artificial Sequence
<220> FEATURE:
<223> OTHER INFORMATION: amyloid peptide

<400> SEQUENCE: 3

Phe Tyr Thr Gly Ala Ile Ile Gly Asn Tyr Phe
1               5                   10

<210> SEQ ID NO 4
<211> LENGTH: 11
<212> TYPE: PRT
<213> ORGANISM: Artificial Sequence
<220> FEATURE:
<223> OTHER INFORMATION: amyloid peptide

<400> SEQUENCE: 4

Tyr Phe Thr Gly Ala Ile Ile Gly Asn Phe Tyr
1               5                   10

<210> SEQ ID NO 5
<211> LENGTH: 11
<212> TYPE: PRT
<213> ORGANISM: Artificial Sequence
<220> FEATURE:
<223> OTHER INFORMATION: amyloid peptide

<400> SEQUENCE: 5

Tyr Phe Thr Gly Ala Ile Ile Gly Asn Tyr Phe
1               5                   10

<210> SEQ ID NO 6
<211> LENGTH: 11
<212> TYPE: PRT
<213> ORGANISM: Artificial Sequence
<220> FEATURE:
<223> OTHER INFORMATION: amyloid peptide

<400> SEQUENCE: 6

Tyr Ala Thr Gly Ala Ile Ile Gly Asn Ile Ile
1               5                   10
```